US012779209B2

(12) United States Patent
Lo et al.

(10) Patent No.: US 12,779,209 B2
(45) Date of Patent: Nov. 3, 2026

(54) ZUSANLI (ST-36) LOCATING TRANSCUTANEOUS ELECTRICAL NERVE STIMULATION AND THERMAL MODALITIES DELIVERING DEVICE FOR TREATING OSTEOARTHRITIC PAIN

(71) Applicant: THE HONG KONG POLYTECHNIC UNIVERSITY, Hong Kong (CN)

(72) Inventors: Chun-Lap Samuel Lo, Hong Kong (CN); Wing-Tak Wong, Hong Kong (CN); Sze Lung Kenneth Chan, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 155 days.

(21) Appl. No.: 18/842,092

(22) PCT Filed: Jun. 20, 2022

(86) PCT No.: PCT/CN2022/099663
§ 371 (c)(1),
(2) Date: Aug. 28, 2024

(87) PCT Pub. No.: WO2023/184723
PCT Pub. Date: Oct. 5, 2023

(65) Prior Publication Data
US 2025/0177729 A1 Jun. 5, 2025

(30) Foreign Application Priority Data
Jun. 20, 2022 (WO) ................ PCT/CN2022/083913

(51) Int. Cl.
*A61N 1/04* (2006.01)
*A61H 39/00* (2006.01)
*A61N 1/36* (2006.01)

(52) U.S. Cl.
CPC ......... *A61N 1/0456* (2013.01); *A61H 39/002* (2013.01); *A61N 1/0476* (2013.01);
(Continued)

(58) Field of Classification Search
None
See application file for complete search history.

(56) References Cited

U.S. PATENT DOCUMENTS 6,445,955 B1 * 9/2002 Michelson ........... A61N 1/0456 607/46
9,020,590 B1 * 4/2015 Honeycutt ............. A61N 1/326 600/27
(Continued)

FOREIGN PATENT DOCUMENTS

CN 101862506 A * 10/2010 ............... A61N 1/32
CN 204193314 U * 3/2015
(Continued)

OTHER PUBLICATIONS

D.M. Walsh, Transcutaneous electrical nerve stimulation and acupuncture points, Complementary Therapies in Medicine (Year: 1996).*
(Continued)

*Primary Examiner* — Manolis Pahakis
(74) *Attorney, Agent, or Firm* — S&F/WEHRW

(57) ABSTRACT

A knee mounting device for providing TENS treatment is disclosed. The knee mounting device is coupled to a patient's knee to locate and stimulate ST-36 acupoint transcutaneously for treating or relieving osteoarthritic pain. The knee mounting device includes a lower assembly mountable onto a leg portion under a kneecap, an upper assembly mountable on a thigh, and a sleeve adapted to connect the upper and lower assemblies. The lower assembly contacts arranged for contacting the ST-36 acupoint, and thermal pad
(Continued)

arranged for applying thermal treatment to an area proximate to the ST-36 acupoint. The upper assembly includes a pulse width modulation (PWM) generator configured to generate a pulse stimulation signal and couple the pulse stimulation signal to the contacts for stimulating the ST-36 acupoint. The sleeve is provided with a kneecap opening located to enwrap the patient's knee as anchor and place the contacts on top of the ST-36 acupoint.

14 Claims, 11 Drawing Sheets

(52) U.S. Cl.
CPC ....... *A61N 1/0484* (2013.01); *A61N 1/36025* (2013.01); *A61N 1/36034* (2017.08)

(56) References Cited

U.S. PATENT DOCUMENTS 9,629,742 B2 * 4/2017 Liu ........................ A61N 1/321
10,610,696 B1 * 4/2020 Peled ..................... A61N 1/403
10,682,512 B1 * 6/2020 Feinstein ............... A61N 1/323
10,953,225 B2 * 3/2021 Druke .................. A61N 1/3603
11,229,789 B2 * 1/2022 Spurling .............. A61B 5/0531
11,458,311 B2 * 10/2022 Loh .................... A61N 1/36007
11,730,958 B2 * 8/2023 Druke .................. A61N 1/0456 607/46
12,575,780 B2 * 3/2026 Hamner ................... A43B 3/34
2002/0138116 A1 * 9/2002 Bertolucci ......... A61N 1/36017 607/72
2005/0085879 A1 * 4/2005 Ahn ..................... A61H 39/002 607/96
2008/0027509 A1 1/2008 Andino et al.
2009/0112278 A1 * 4/2009 Wingeier ............. A61B 5/4076 607/45
2011/0288610 A1 * 11/2011 Brocke ................. A61M 21/02 607/45
2012/0016446 A1 1/2012 Panting
2013/0030277 A1 * 1/2013 Fahey .................. A61N 1/0476 607/48
2013/0085317 A1 * 4/2013 Feinstein ........... A61N 1/37247 600/14
2014/0074000 A1 * 3/2014 Liu ...................... A61N 1/0502 602/2
2016/0045733 A1 * 2/2016 Mcgeoch ........... A61N 1/36031 607/148
2017/0165485 A1 6/2017 Sullivan et al.
2017/0304616 A1 * 10/2017 McGeoch .......... A61N 1/36014
2018/0114465 A1 * 4/2018 Eikefjord ............... A61N 1/046
2018/0221651 A1 * 8/2018 Chang .................... B23K 26/40
2019/0255324 A1 * 8/2019 Masuda ............. A61N 1/36021
2019/0321636 A1 * 10/2019 Law ................... A61N 1/36034
2019/0381313 A1 * 12/2019 Lu ............................ A61N 2/02
2020/0147378 A1 * 5/2020 Thomas-Soriot ...... A61N 1/048
2020/0246616 A1 8/2020 Simon et al.
2020/0282227 A1 * 9/2020 Guan ................... A61N 1/3603
2020/0297244 A1 * 9/2020 Brownhill ............ A61B 5/1032
2020/0306536 A1 10/2020 Wang
2020/0338333 A1 * 10/2020 Toong .................. A61N 1/0492
2020/0338334 A1 * 10/2020 Toong .................. A61N 1/0476
2020/0360653 A1 * 11/2020 McKeown ............ A61M 21/02
2020/0398053 A1 * 12/2020 Li ....................... A61N 1/36034
2021/0016087 A1 * 1/2021 Shahriari ........... A61N 1/36003
2021/0023360 A1 * 1/2021 Toong .................. A61N 1/0456
2021/0046312 A1 * 2/2021 McKeown ........... A61N 1/0456
2021/0100998 A1 * 4/2021 Charlesworth ........ A61B 5/395
2021/0101007 A1 * 4/2021 Hamner ............. A61N 1/36007
2021/0205619 A1 * 7/2021 Wong ................. A61N 1/36007
2021/0260376 A1 * 8/2021 Rhodes .................... A61B 5/01
2021/0283400 A1 * 9/2021 Hamner ............... A61N 1/0456
2022/0143391 A1 * 5/2022 Vaishya ............... A61N 1/0484
2022/0233848 A1 * 7/2022 Gad ..................... A61N 1/0551
2022/0273947 A1 * 9/2022 Law .................... A61N 1/36034
2023/0173278 A1 * 6/2023 Wang ................. A61N 1/36034
2023/0338136 A1 * 10/2023 Howard ............... A61N 1/0456
2024/0130672 A1 * 4/2024 Cardasis .............. A61B 5/4836
2024/0198122 A1 * 6/2024 Borkum ................. A61B 5/316

FOREIGN PATENT DOCUMENTS

CN 206044967 U * 3/2017
CN 106823144 A * 6/2017 ......... A61N 1/36014
CN 206341989 U * 7/2017
CN 109069828 A 12/2018
CN 109199670 A 1/2019
CN 112206416 A 1/2021
CN 112601488 A 4/2021
CN 113101518 A 7/2021
CN 113631219 A 11/2021
EP 2383014 A1 * 11/2011 ........... A61N 1/0476
JP S6428657 U 2/1989
KR 20230168315 A * 12/2023 ......... A61N 1/36014
WO WO-2016197039 A1 * 12/2016 ......... A61N 1/36053
WO WO-2019143307 A2 * 7/2019 ........... A61N 1/0484
WO WO-2020088422 A1 * 5/2020 ............. A61H 39/00

OTHER PUBLICATIONS

Clarivate Analytics, Translation of CN-101862506-A (Year: 2026).*
Clarivate Analytics, Translation of CN-106823144-A (Year: 2026).*
Clarivate Analytics, Translation of CN-204193314-U (Year: 2026).*
Clarivate Analytics, Translation of CN-206044967-U (Year: 2026).*
Clarivate Analytics, Translation of CN-206341989-U (Year: 2026).*
Clarivate Analytics, Translation of KR-20230168315-A (Year: 2026).*
Clarivate Analytics, Translation of WO-2020088422-A1 (Year: 2026).*
Extended European Search Report; PCT Application No. Application PCT/CN2022083913 Issued from the European Patent Office on Sep. 2, 2025.
Notice of Reasons for Refusal of Japanese Patent No. 2024-553426 issued from the Japan Patent Office on Sep. 22, 2025.
Office Action of TW 112109967 issued from the Taiwan International Patent & Law Office (TIPLO) on Feb. 19, 2015.

* cited by examiner

ZUSANLI (ST-36) LOCATING TRANSCUTANEOUS ELECTRICAL NERVE STIMULATION AND THERMAL MODALITIES DELIVERING DEVICE FOR TREATING OSTEOARTHRITIC PAIN

FIELD OF THE INVENTION

The present disclosure generally relates to a knee mounting device that locate the acupuncture point Zusanli (ST-36) accurately for layman for treating osteoarthritic pain. In particular, the present disclosure relates to a constant current transcutaneous electrical nerve stimulation (TENS) knee mounting device with thermal delivering modalities that can be mounted accurately onto the ST-36 acupuncture point. The device is mounted onto the knee via the kneecap to enable ST-36 acupoint of an adult patient to be located accurately. The TENS and thermal modalities can stimulate the ST-36 acupoint for treating or relieving osteoarthritic pain.

BACKGROUND OF THE INVENTION

Osteoarthritis is a degenerative disease characterized by the gradual destruction of the articular cartilage and periarticular structures, such as bones, synovial, and the associated fibrous joint tissues when a person gets older. With less and less cushioning benefits of cartilage and synovial fluid, bones of the joints would begin to rub against each other more. This rubbing will lead to degeneration of the joints and is usually manifested as pain, swelling, stiffness, and decreased ability to move. More wear-and-tear in the joints is resulted. In addition, bone spurs would be commonly formed. This condition is collectively called arthritis.

Reports from the World Health Organization (WHO) estimated that osteoarthritis is present in approximately 30% of men and women over the age of 65.2. From another perspective, for people over 60 years of age, worldwide estimates are that 9.6% of men and 18.0% of women have osteoarthritis [1]. According to the Arthritis Foundation, more than 27 million people in the U.S. have osteoarthritis, and most of them are elderly [2]. It was also found that women are more likely to have osteoarthritis than men. The severity of osteoarthritis will increase with age, weight, repetitive stress injuries, excessive iron loads on the body, and excessive growth hormone.

In 2004, Lee et al. reported that among Hong Kong patients, the direct cost of treatment of osteoarthritic pain was approximately between HK$11,690 to HK$40,180 per person per year [3]. Given the ever-increasing aging population in Hong Kong and nationally, the demand for treatment is expected to continue to increase. Standard pharmacological treatment of osteoarthritis is through the use of analgesics (painkillers) and/or nonsteroidal anti-inflammatory drugs (NSAIDs) for reducing pain and inflammation. Short-term use of analgesics may have adverse side effects, such as an upset stomach, dry mouth, constipation, fatigue, rash, itching, nausea, and shallow breathing [4]. However, there are other long-term side effects, including heart, lung, and liver problems, stomach ulcers, allergies, extreme sedation, high blood pressures, elevated risk of vascular thrombosis, dependency, and withdrawal symptoms. Therefore, long-term uses of such medicines are not recommended and other alternative non-invasive treatments, such as message and the use of transcutaneous electrical nerve stimulation (TENS) device, had been proposed to treat osteoarthritic pain.

Message treatment, although enjoyable, usually has no lasting effect. On the other hand, TENS is a therapeutic procedure involving the use of electric current to stimulate peripheral nerves underneath the skin. It is believed that TENS, being non-invasive, has relatively minimal side effects. However, there are two issues with TENS treatment.

Firstly, a lot of TENS treatments use simple TENS-delivery machines which usually give TENS pulses via constant voltage. After TENS treatment starts, concomittment muscular contraction will eventually lead to increased muscular resistance. Therefore, if the TENS device uses a constant voltage approach, the TENS current would diminish with the progression of TENS treatment and the therapeutic effects nullified eventually. To provide undiminished TENS current, constant TENS current mode should be used. A simple TENS delivery machine cannot provide constant TENS current as the device needs to measure the TENS current output continuously. Hence, to provide a persistent therapeutic effect, a TENS machine that can provide constant current is needed.

Secondly, in the practice of traditional Chinese medicine, TENS has to be administrated on acupuncture points (acupoints) to achieve special and designated therapeutic effects. However, besides possibly providing a diagram, most of the TENS devices would not provide additional help to users to locate the acupuncture points accurately. People have different heights and dimensions and hence the location of the acupoints varied accordingly. Therefore, it is necessary to have a professional acupuncturist to locate the acupoints. Further, in the practice of traditional Chinese medicine, additional thermal modalities on the acupuncture points and associated areas can also be therapeutic and alleviate the pain sensation. Many of the over-the-counter TENS devices that are battery operated do not have this provision.

In the U.S. Pat. No. 8,855,759 B2, inventor of the present disclosure successfully reduced the pain during the constant current TENS treatment with topical application of ginsenosides. The invention is specifically related to a method of treating rheumatic disorders, and symptoms of arthritis. The method involves using TENS and a combination with the administration of a ginsenoside, such as Rb1. In one example, TENS was applied first onto two acupuncture points, ST-35 and EX-LE-4, because they are common local points for treating knee problems. Rb1 was administrated after TENS treatment. In a rat model, the combined synergistic effects of TENS/Rb1 increased the concentrations of interleukin-10 (IL-10), IL-2, IL-1-alpha, and IL-1-beta. All these internal secretions dampen the heightened levels of inflammation in the body so as to reduce the corresponding swelling and pain. However, clinical trial on the previously patented invention has not be performed.

Accordingly, there is a need in the art to have a device and a method for stimulating the acupoint for treating osteoarthritic pain. Furthermore, other desirable features and characteristics will become apparent from the subsequent detailed description and the appended claims, taken in conjunction with the accompanying drawings and this background of the disclosure.

SUMMARY OF THE INVENTION

Provided herein are a knee mounting device to accurately locate ST-36 acupoint and a method for stimulating the acupoint for treating osteoarthritic pain. It is the objective of the present disclosure to provide stimulation to the selected acupoint for treating or relieving osteoarthritic pain. It is also desirable to have the acupoint located accurately and properly stimulated to achieve the intended benefits to the patient.

In the first aspect of the invention, there is provided a knee mounting device for providing TENS treatment is disclosed. The knee mounting device is coupled to a patient's knee via the kneecap to locate and stimulate Zusanli (ST-36) acupoint of the patient transcutaneously for treating or relieving osteoarthritic pain. The knee mounting device includes a lower assembly mountable onto a leg portion under a kneecap of the patient, an upper assembly mountable on a thigh of the patient, and a sleeve adapted to connect the upper assembly and the lower assembly. The lower assembly includes a plurality of contacts arranged on an underside of the lower assembly for contacting the ST-36 acupoint on the lower leg, and one or more thermal pads arranged on the underside of the lower assembly for applying thermal treatment to an area proximate to the ST-36 acupoint. The upper assembly includes a pulse width modulation (PWM) generator configured to generate a pulse stimulation signal and couple the pulse stimulation signal to the plurality of contacts for stimulating the ST-36 acupoint. The sleeve is provided with a kneecap opening located to enwrap the patient's knee and place the plurality of contacts on top of the ST-36 acupoint.

In an embodiment, the plurality of contacts includes a first contact pad and a second contact pad, wherein the first contact pad is electrically connected to the PWM generator for coupling the pulse stimulation signal, and the second contact pad is electrically connected to a low reference voltage.

In an embodiment, the kneecap opening receives the kneecap when the knee mounting device is worn by the patient for defining an anchor position, and the first and the second contact pads are positioned relative to the anchor position, to contact the ST-36 acupoint.

In an embodiment, the first and the second contact pads are dimensioned to cover individual variations of locations of the ST-36 acupoint, with the second contact pad being larger than the first contact pad.

In an embodiment, the pulse stimulation signal has a constant current of not more than 120 μA, and preferably the constant current is between 20 μA and 60 μA, thereby therapeutic effects are not affected upon continuous use of the knee mounting TENS device.

In an embodiment, the pulse stimulation signal is a square wave with a pulse width of 50 milli-second to 200 milli-second, and preferably the pulse width is between 100 milli-second and 120 milli-second.

In an embodiment, each of the one or more thermal pads includes a winding of a thermally conductive material for delivering thermal energy to the ST-36 acupoint and the area proximate to the ST-36 acupoint with a temperature up to 40° C.

In an embodiment, the knee mounting device further includes one or more temperature sensors for obtaining temperature readings of areas proximate to the one or more thermal pads and areas underneath the knee mounting device; a current sensor for detecting an electric current flowing through the patient via the plurality of contacts; and a processor provided in the upper assembly, wherein the processor is configured to monitor and adjust the one or more thermal pads and the PWM generator continuously based on the temperature readings detected by the one or more temperature sensors and the electric current detected by the current sensor.

In an embodiment, the upper assembly includes a Bluetooth module configured to operate according to the Bluetooth wireless protocol for transmitting and receiving wireless signals.

In an embodiment, the upper assembly and the lower assembly are electrically connected together using flexible cables.

In an embodiment, the upper assembly and the lower assembly each includes fastening means for applying a tension to hold the upper assembly and the lower assembly on the thigh and the lower leg of the patient respectively, wherein the fastening means comprise a strap and a strap fastener.

In an embodiment, the sleeve is made of an elastic material selected from the group consisting of natural rubber, silicone, latex, nylon, elastic textile, and cotton.

In an embodiment, the sleeve is dimensioned to partially cover or encircle the kneecap and to allow an accurate locationization of the ST-36 acupoint.

In an embodiment, the knee mounting device further includes a vibrator arranged on the underside of the lower assembly for providing psychological effects to the patient.

In the second aspect of the invention, there is provided a TENS device adapted to stimulate the ST-36 acupoint of a patient transcutaneously for treating or relieving osteoarthritic pain. The TENS device includes a sleeve having a kneecap opening located to enwrap the patient's knee and place the plurality of contacts on top of the ST-36 acupoint; a plurality of contacts arranged on an underside of the sleeve for contacting the ST-36 acupoint on the lower leg; a PWM generator configured to generate a pulse stimulation signal and couple the pulse stimulation signal to the plurality of contacts for stimulating the ST-36 acupoint; and one or more thermal pads arranged on the underside of the sleeve for applying thermal treatment to an area proximate to the ST-36 acupoint.

In an embodiment, the plurality of contacts includes a positive terminal and a negative terminal, wherein the positive terminal is electrically connected to the PWM generator for coupling the pulse stimulation signal, and the negative terminal is electrically connected to a low reference voltage.

In an embodiment, the kneecap opening receives the kneecap when the sleeve is worn by the patient for defining an anchor position, and the positive and negative terminals are positioned relative to the anchor position to contact the ST-36 acupoint.

In an embodiment, the positive and negative terminals are dimensioned to cover individual variations of location of the ST-36 acupoint, with the negative terminal being physically larger than the positive terminal.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects and advantages of the present invention are disclosed as illustrated by the embodiments hereinafter.

BRIEF DESCRIPTION OF THE DRAWINGS

The appended drawings contain figures to further illustrate and clarify the above and other aspects, advantages, and features of the present disclosure. It will be appreciated that these drawings depict only certain embodiments of the present disclosure and are not intended to limit its scope. It will also be appreciated that these drawings are illustrated for simplicity and clarity and have not necessarily been depicted to scale. The present disclosure will now be described and explained with additional specificity and detail through the use of the accompanying drawings in which.

DETAILED DESCRIPTION OF THE INVENTION

Figure 1:
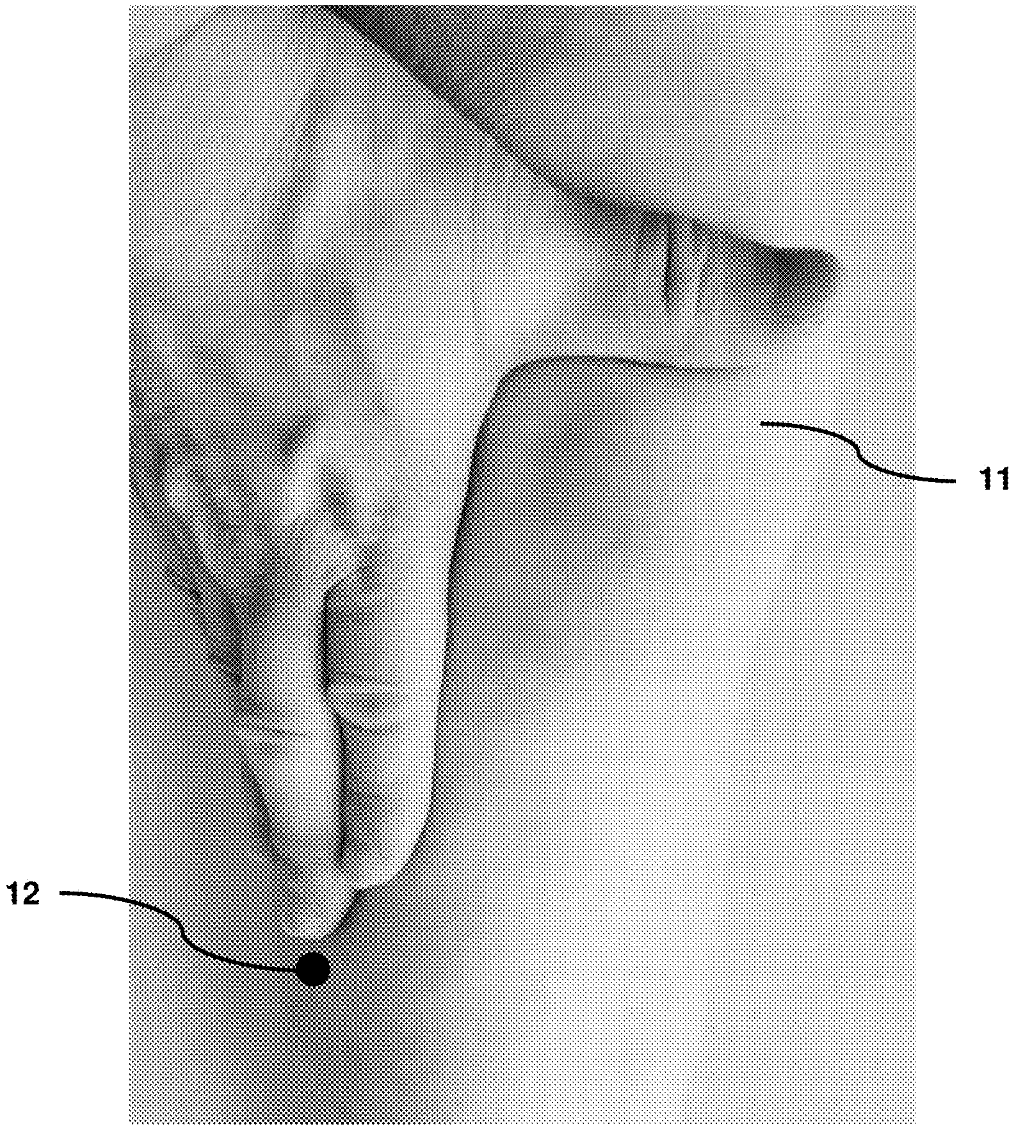
FIG. 1 shows a photo highlighting the location of the acupoint Zusanli (ST-36), in which this acupoint may provide beneficial effects to a patient suffering from osteoarthritic pain when appropriately stimulated.

The present disclosure generally relates to a device and a method for treating osteoarthritic pain. More specifically, but without limitation, the present disclosure provides a constant current transcutaneous electrical nerve stimulation (TENS) device with thermal modalities that can be mounted on the knee of a patient with the kneecap as the anchor, for stimulating the acupoint for treating or relieving osteoarthritic pain. It is the objective of the present disclosure to provide stimulation to the selected acupoint near the knee joint of a patient for treating or relieving osteoarthritic pain.

The present disclosure provides a safe and reliable means for treating or relieving osteoarthritic pain. As discussed in the previous sections, osteoarthritis is a degenerative disease characterized by the gradual destruction of the articular cartilage and periarticular structures. The use of TENS treatment is a proven therapy for providing beneficial effects to patients, which can provide both long-term and short-term improvements on reducing osteoarthritic pain. This device of the present disclosure is designed for the convenience of the caregiver and the patient. Most importantly, the device is non-invasive, and the use is essentially painless. The caregiver can conveniently put the device on the knee of the patient. Additionally, the data collected can be streamed back using wireless communication for caregivers, medical practitioners, or therapists to gauge the treatment conditions and/or progress of condition of the patient.

The benefits, advantages, solutions to problems, and any element(s) that may cause any benefit, advantage, or solution to occur or become more pronounced are not to be construed as critical, required, or essential features or elements of any or all of the claims. The invention is defined solely by the appended claims including any amendments made during the pendency of this application and all equivalents of those claims as issued.

In the claims which follow and in the preceding description of the invention, except where the context requires otherwise due to express language or necessary implication, the word "comprise" or variations such as "comprises" or "comprising" is used in an inclusive sense, i.e., to specify the presence of the stated features but not to preclude the presence or addition of further features in various embodiments of the invention. As used herein, the term "proximate" when used in relation to a position refers to an area within +/−2 centimeters of the position, and preferably within +/−1 centimeter of the position.

As used herein and in the claims, "couple" or "connect" refers to electrical coupling or connection either directly or indirectly via one or more electrical means unless otherwise stated. The recitation of ranges of values herein is not intended to be limiting, but rather relates individually to any and all values falling within the range, unless otherwise indicated herein.

The present disclosure is based on the doctrine of acupuncture, which is an alternative medicine that treats patients by insertion and manipulation of needles in the body at selected locations. As used herein and in the claims, the acupoints, or sometimes referred to as "acupuncture points", are those selected locations in the human body. Generally, the acupoints are identified by a name followed by a reference formed by a combination of letters and a number. From the reference, the body organ or tissue location associated with, or affected by, that acupoint can be identified.

As used herein and in the claims, "transcutaneous electrical nerve stimulation" or "TENS" may refer to the therapeutic procedure involving the use of electric current to stimulate peripheral nerves underneath the skin. If the location of stimulation is selected in accordance with the traditional acupuncture therapy, the therapy may be referred to as electroacupuncture. Traditional acupuncture requires the insertion of thin needles very accurately through the skin at the acupoints. TENS device of the present disclosure is not using such thin needles, instead, some electrodes or contact pads are placed on the skin for stimulation.

As shown in FIG. 1, the location of the Zusanli (ST-36) acupoint 12 is on the anterior aspect of the lower leg, which is 3 cun below the Dubi (ST-35) acupoint. Generally, the ST-36 acupoint 12 can be easily located by measuring the finger breadth of the middle finger from the anterior crest of the tibia. In the literature, the therapeutic effects of simulating the ST-36 acupoint 12 are associated with a decrease in inflammation, and an improvement in insulin sensitivity and cerebral blood flow. The present disclosure provides that the ST-36 acupoint 12 is relevant to the treatment of osteoarthritic pain, which is potentially capable of providing stimulation to the patients suffering from osteoarthritis.

In the practice of Chinese medicine, the acupoints may provide beneficial effects to the patient when appropriately stimulated. Comparing to the use of thin needles in traditional practice of acupuncture, the use of TENS treatment on selected acupoints can achieve even better designated therapeutic effects. It is because there is no skin puncture, the operation can be performed by the caregivers without the need of a professional acupuncturist. However, the accuracy in contacting and stimulating the acupoints should not be sacrificed. The present disclosure provides a knee mounting device that is designed to locate ST-36 easily and hence stimulate the ST-36 acupoint 12. The knee mounting device is structured to accurately fit the TENS electrodes and thermal pads above the ST-36 acupoint 12 and the area proximate to the ST-36 acupoint 12, and provide stimulation to the patient.

As one would imagine, a person comes with different heights, built and sizes, etc. Hence, the location of the ST-36 acupoint 12 may vary from person to person. That is why it is difficult for laymen to find the ST-36 acupoint 12 themselves. One of the advantages of the present disclosure provides a device that allows the caregiver or the patient to locate and stimulate the ST-36 acupoint 12 easily without the help of a professional acupuncturist.

Figure 2:
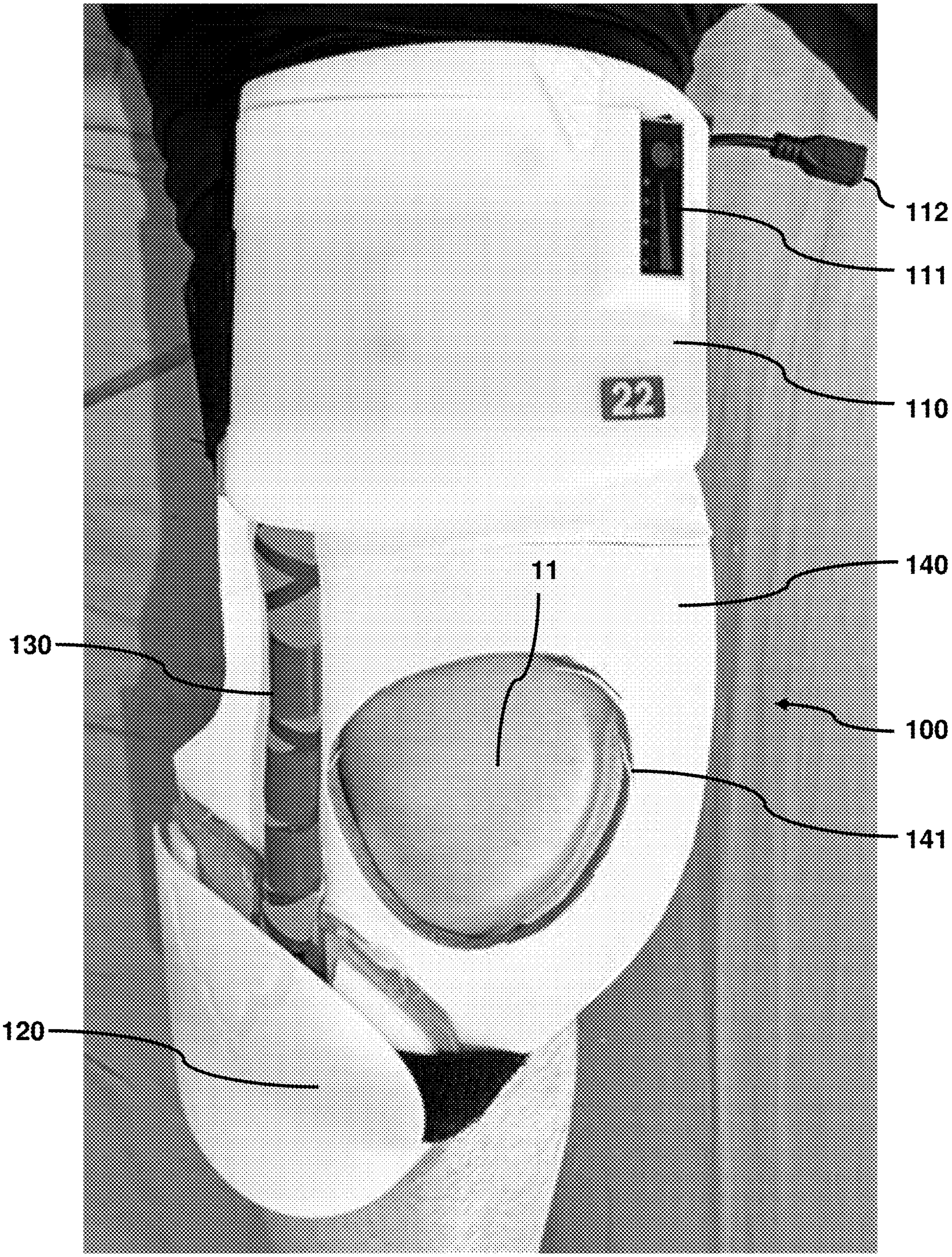
FIG. 2 shows a photo of a patient wearing an exemplary knee mounting device on the right leg for treating osteoarthritic pain in accordance with certain embodiments of the present disclosure.
Figure 3:
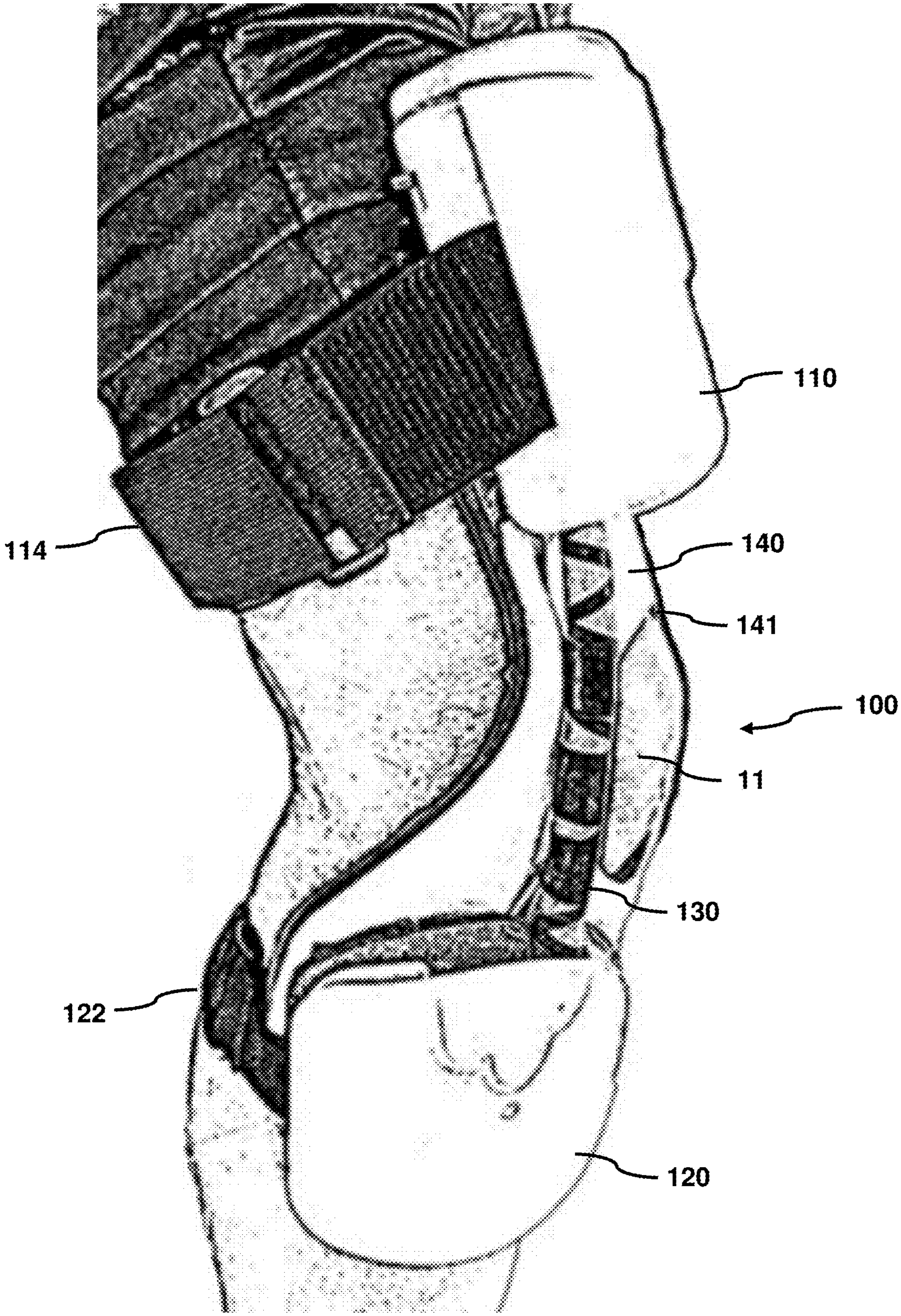
FIG. 3 shows a side view of FIG. 2.
Figure 4:
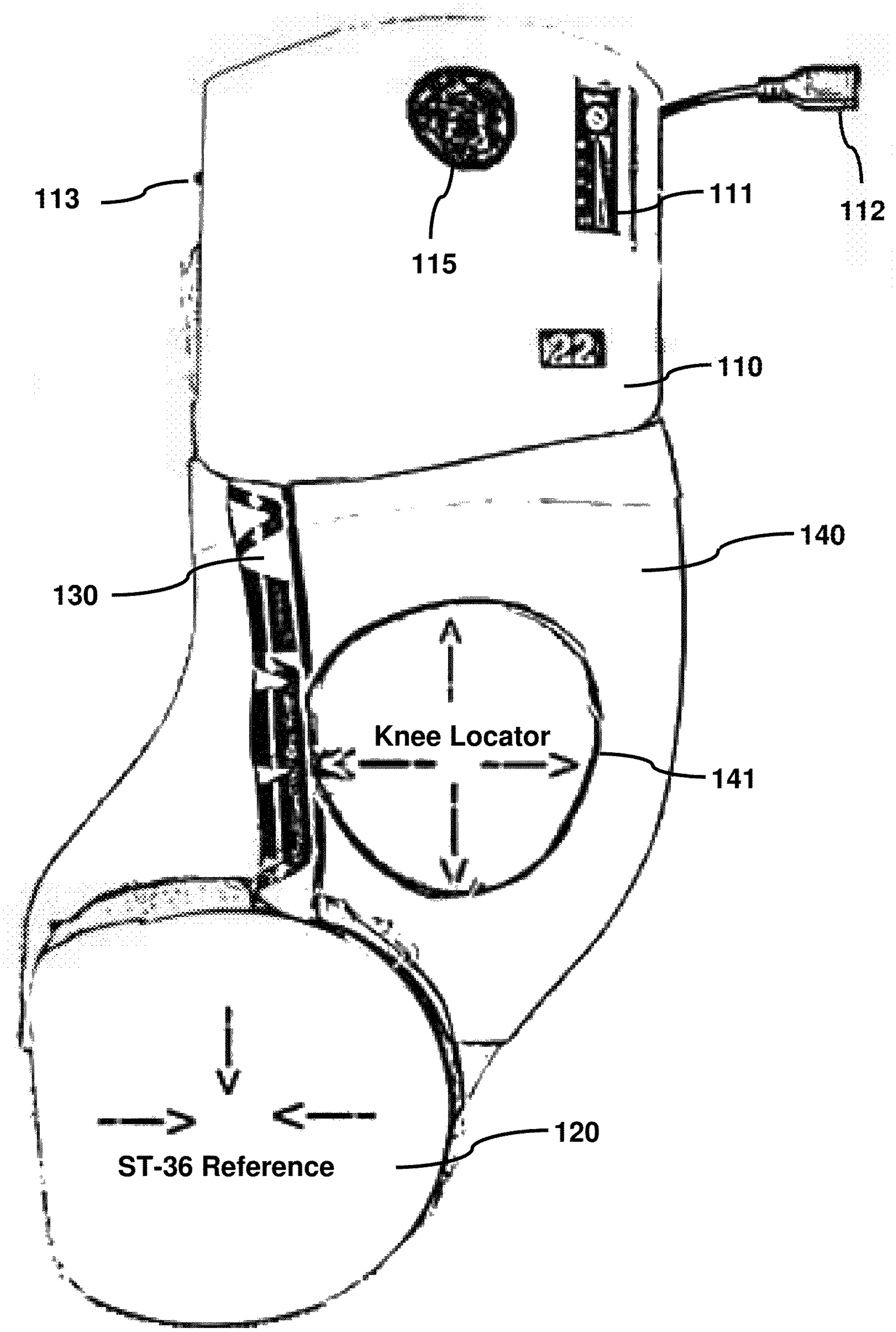
FIG. 4 shows an exemplary knee mounting device for treating osteoarthritic pain in accordance with certain embodiments of the present disclosure.

As shown in FIGS. 2-4, a knee mounting device 100 is fabricated as a very user-friendly wearable device that may be used by patients suffering from osteoarthritis or other joint disorder and musculoskeletal pain conditions. The knee mounting device 100 is adapted to stimulate the ST-36 acupoint 12 of a patient transcutaneously for treating or relieving osteoarthritic pain when being worn on the lower body of the patient. Particularly, the knee mounting device 100 uses the kneecap (patella) 11 of the patient as an anchor for identifying the correct location of the ST-36 acupoint 12. By putting on the knee mounting device 100 properly, the TENS electrodes would be placed accurately on top of the ST-36 acupoint 12 without any professional help. Therefore, it is possible for a layman caregiver to use the knee mounting device 100 to provide stimulation on the acupoint for treating or relieving osteoarthritic pain.

Although throughout the specification, a knee mounting device 100 is described for coupling to a patient's knee for treating or relieving osteoarthritic pain, it is apparent that the present invention may also be implemented otherwise as other TENS devices (hereinafter referred to as "TENS device") adapted to stimulate the ST-36 acupoint 12 of a patient transcutaneously for treating or relieving osteoarthritic pain. The TENS device may not conform to the mechanical details and illustrated structures, and thus, could be integrated with other wearable devices or garments (such as trousers).

The knee mounting device 100 may comprise a lower assembly 120, an upper assembly 110, and a sleeve 140. The lower assembly 120 is mountable onto a leg portion under the kneecap 11 of the patient, and includes a plurality of contacts 620 (shown in FIG. 6) arranged on an underside of the lower assembly 120 for contacting the ST-36 acupoint 12 on the lower leg, and one or more thermal pads 630 (shown in FIG. 6) arranged on an underside of the lower assembly 120 for applying thermal treatment to an area proximate to the ST-36 acupoint 12. The illustrated embodiment shows a knee mounting device 100 for use with the right leg. In the practice of acupuncture of traditional Chinese medicine, stimulation of the appropriate nervous system can bring effects not just to the parts administrated, but also all over the body. Therefore, stimulating the ST-36 acupoint 12 on the right leg can produce overall beneficial effects to the whole body of the patient. Given this background, although the present disclosure provides a knee mounting device 100 for mounting onto the right leg, it is apparent that this arrangement is not restrictive and the knee mounting device 100 may otherwise be designed to be mounted onto the left leg for providing stimulation of the ST-36 acupoint 12 on the left leg, without departing from the scope and spirit of the present disclosure.

In the illustrated embodiment, the upper assembly 110 includes the controlling unit configured to control the plurality of contacts 620 and the one or more thermal pads 630 at the lower assembly 120. The upper assembly 110 and the lower assembly 120 are electrically connected together using electrical wirings or flexible cables 130, which should be securely packed within plastic insulating material to protect the electrical wirings or flexible cables 130 from damage and deterioration upon prolonged use. It is apparent that the knee mounting device 100 may be structured without the upper assembly 110, and the controlling unit is alternatively provided in the lower assembly 120, and such an alternative structure is not departed from the scope and spirit of the present disclosure.

The sleeve 140 is made of elastic material selected from the group consisting of natural rubber, silicone, latex, nylon, elastic textile, and cotton. Although the knee mounting device 100 can provide some protection because of its setup, it is not intended to provide joint protection for sports use or constant wearing. Therefore, the knee mounting device 100 of the present disclosure shall not be used or function as protective wear for the knee. The sleeve 140 is dimensioned to partially cover or encircle the patient's kneecap 11 as anchor and to allow an accurate localization of the ST-36 acupoint 12 for the electrodes. On the upper end and the lower end of the sleeve 140, the upper assembly 110 and the lower assembly 120 are connected. The sleeve 140 is further provided with a kneecap opening 141. Precisely, the kneecap opening 141 is disposed over and receives the kneecap 11 to permit the sleeve 140 to align centrally to the kneecap 11 when the knee mounting device 100 is worn by the patient.

In certain embodiments, the upper assembly 110 and the lower assembly 120 each comprises fastening means 114, 122 for applying a tension to hold the upper assembly 110 and the lower assembly 120 on the thigh and the lower leg of the patient respectively. The fastening means 114, 122 may include a strap that can be adjusted in length for providing flexibility to adjust to match the size of the patient's lower body, and a strap fastener. It is apparent that the fastening means 114, 122 may also include, for example, zippers, hook-and-loop fasteners, and Velcro.

The knee mounting device 100 further includes a rechargeable battery (not shown), power port 112, battery level indicator 111, light-emitting diode (LED) indicator 115 for indicating the operation, and a power switch 113, provided in the upper assembly 110. The rechargeable battery may be, for example, a lithium-ion battery, a lithium polymer battery, a lithium metal battery, or a nickel-cadmium battery. When charging the rechargeable battery, the power port 112 is supplied with a DC voltage from a regulator or a USB charging device. The power switch 113 is switchable between an on-state and an off-state. During on state, the LED indicator 115 is turned on with color for indicating the status of the knee mounting device 100. In certain embodiments, the LED indicator 115 can alert the caregiver when there is an abnormal operation.

Figure 5:
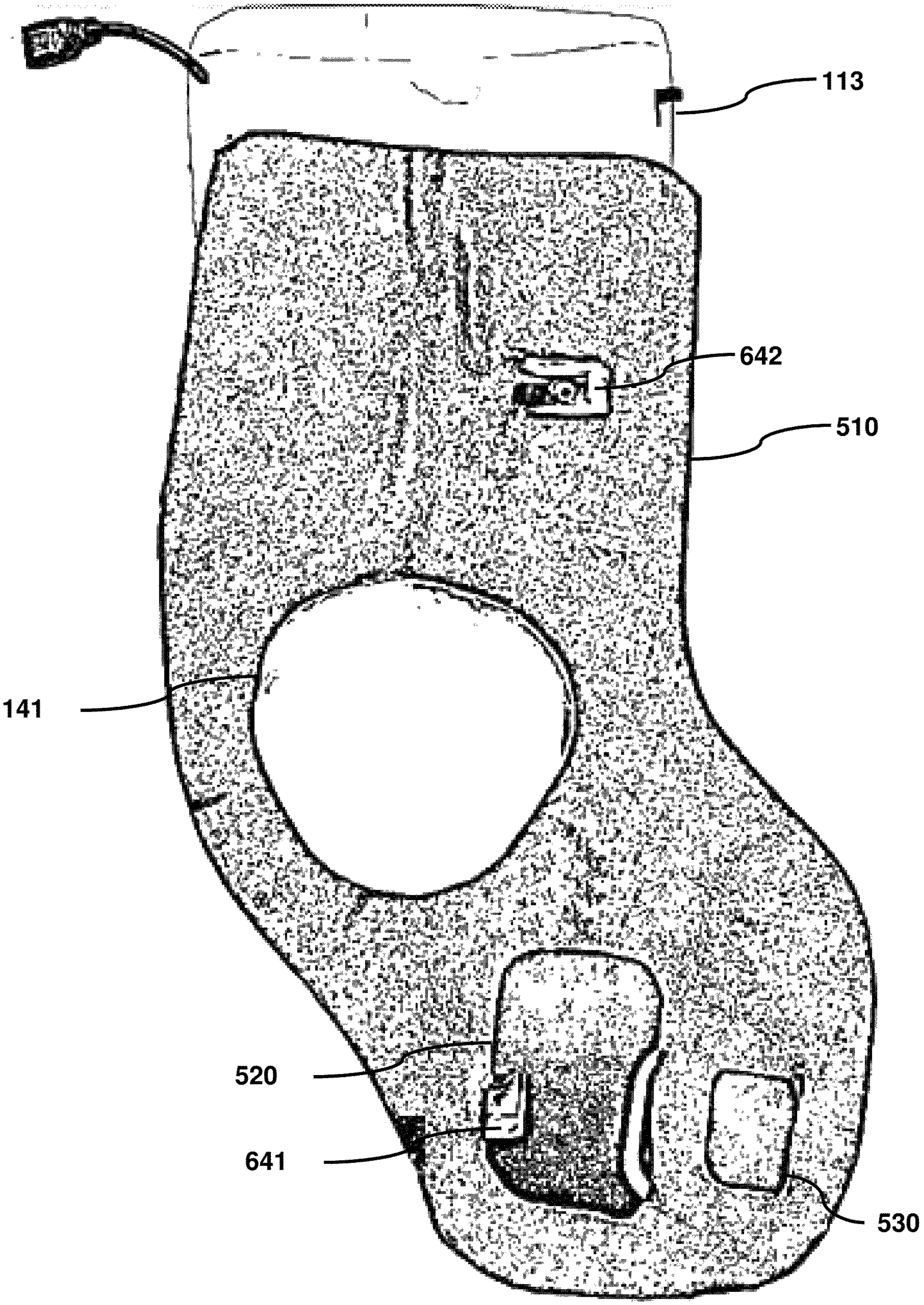
FIG. 5 shows the underside of the knee mounting device of FIG. 4.

Referring to the underside 510 of the knee mounting device 100 in FIG. 5, there is provided a first contact region 520 and a second contact region 530 located at positions beneath the lower assembly 120. Therefore, the first and second contact regions 520, 530 are arranged to directly contact the skin of the patient at areas proximate to the ST-36 acupoint 12. One or more thermal pads 630 are also provided near the first contact region 520, which will be discussed below. One or more temperature sensors 641 are provided near the first contact region 520 for obtaining temperature readings of areas proximate to the one or more thermal pads 630 to ensure that the temperature is within the range of 36° C. and 40° C. A second temperature sensor 642 is provided on the underside 510 of the knee mounting device 100 near the upper assembly 110 for obtaining temperature readings of areas underneath the knee mounting device 100 but not close to the one or more thermal pads 630 to act as control temperature.

Figure 6:
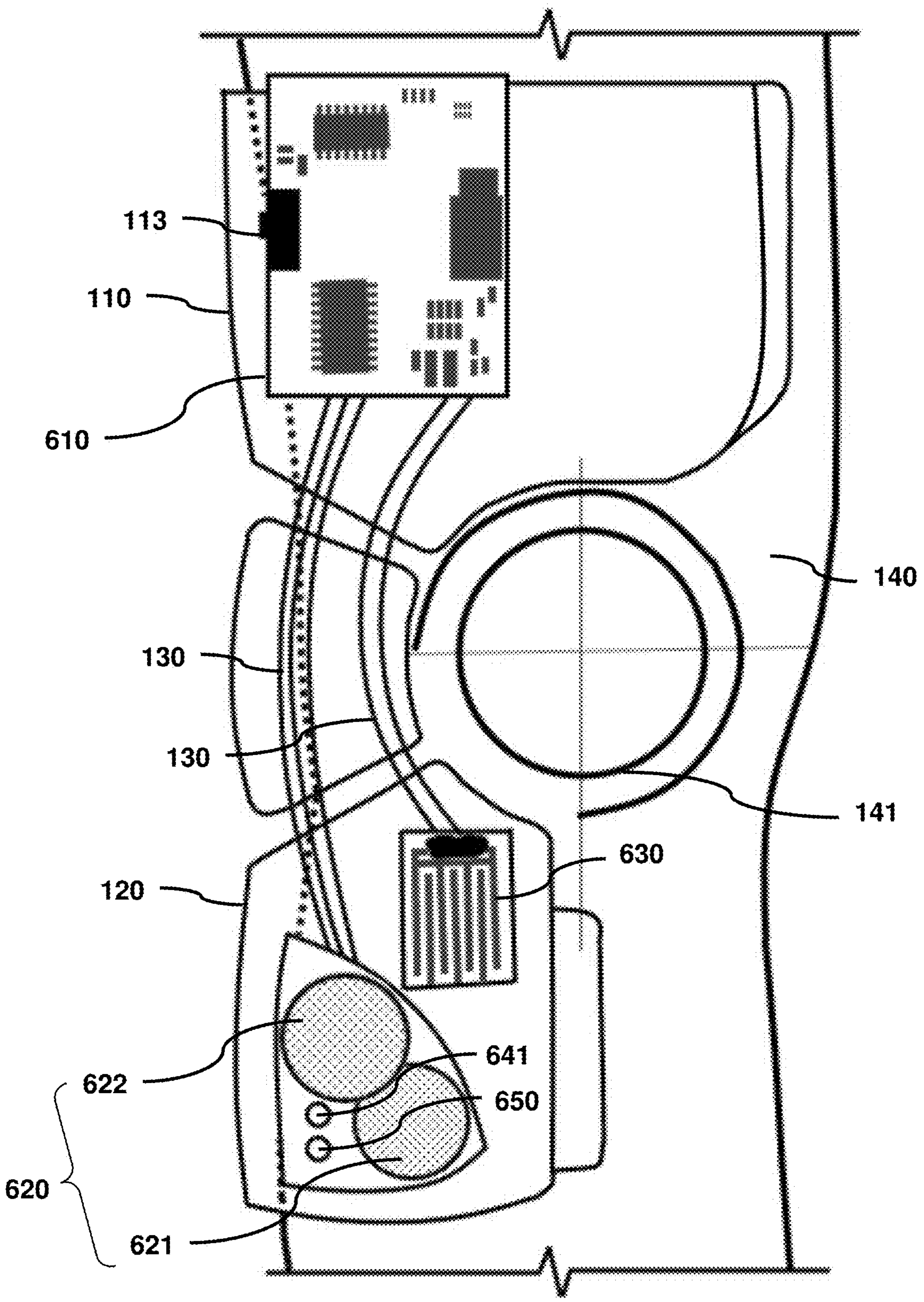
FIG. 6 illustrates the internal structure of the knee mounting device in accordance with certain embodiments of the present disclosure.

FIG. 6 illustrates the internal structure of an exemplary knee mounting device 100 in accordance with the present disclosure. The upper assembly 110 includes at least a circuit board 610 and associated components for controlling the TENS delivery. The circuit board 610 of the upper assembly 110 is electrically connected to the lower assembly 120 using electrical wirings or flexible cables 130 for controlling the plurality of contacts 620 and the one or more thermal pads 630. In the preferred embodiment, the plurality of contacts 300 comprises at least a first contact pad 621 and a second contact pad 622. Optionally and preferably, the second contact pad 622 is larger than the first contact pad 621. For example, the second contact pad 622 is 65 mm×45 mm, and the first contact pad 621 is 30 mm×20 mm. Preferably, the contact pad 410 is a circular plate. Setup and dimensions of the plurality of contact pads 620 could be used to easily and accurately cover variations in the location of the ST-36 acupoint 12 between people of different sizes and heights. With the kneecap opening 141 receiving the kneecap when the knee mounting device 100 is worn by the patient to define an anchoring position, the first contact pad 621 and the second contact pad 622 are positioned relative to the anchor position to contact the ST-36 acupoint 12 accurately.

Another aspect of the present disclosure provides one or more thermal pads 630 for applying thermal modalities to the ST-36 acupoint 12. In the illustrated embodiment, one thermal pad is provided near the first contact pad 621. It is apparent that one or more further thermal pads (not shown) may be provided on the underside of the second assembly 120 without departing from the scope and spirit of the present disclosure.

The one or more thermal pads 630 are electricity generated heating pads configured to deliver heat to the ST-36 acupoint 12 of the patient and areas proximate to the ST-36 acupoint 12. The thermal pad 630 comprises electrical cables and a winding of a thermally conductive material for delivering thermal energy with a temperature up to 40° C. The winding may have a symmetrical routing pattern, a spiral routing pattern, or other patterns. The rise in temperature above the normal body temperature can improve blood circulation around the ST-36 acupoint 12, which can effectively reduce osteoarthritic pain. The thermal pad 630 is sized and positioned to conform to the locations of the acupoint to be stimulated. In certain embodiments, the thermal pad 630 is provided in the same position as the plurality of contacts 620.

In certain embodiments, a vibrator 650 may be provided on the underside 510 of the knee mounting device 100 to contact the skin of the patient. The vibrator 650 is configured to generate vibration stimulation to areas proximate to the ST-36 acupoint 12. The vibration may not substantially produce therapeutic beneficial effects to the patient, but the use of the vibrator 650 is important to provide certain psychological effects. Particularly for those elderly patients, there is a decline in sensation of pain. As a result, the TENS treatment may not cause any noticeable sensation to the patient. Patient suffering from osteoarthritic pain may have the wrong impression that the TENS device is not working or treatment is ineffective. Some other patients may also develop fear and anxiety when they feel nothing while doing the treatment. Therefore, the patient may increase the TENS current to a level less beneficial to the patient. The use of the vibrator 650 to provide mild vibrational stimulation to lessen anxiety of the patient while TENS treatment is in progress.

Figure 7:
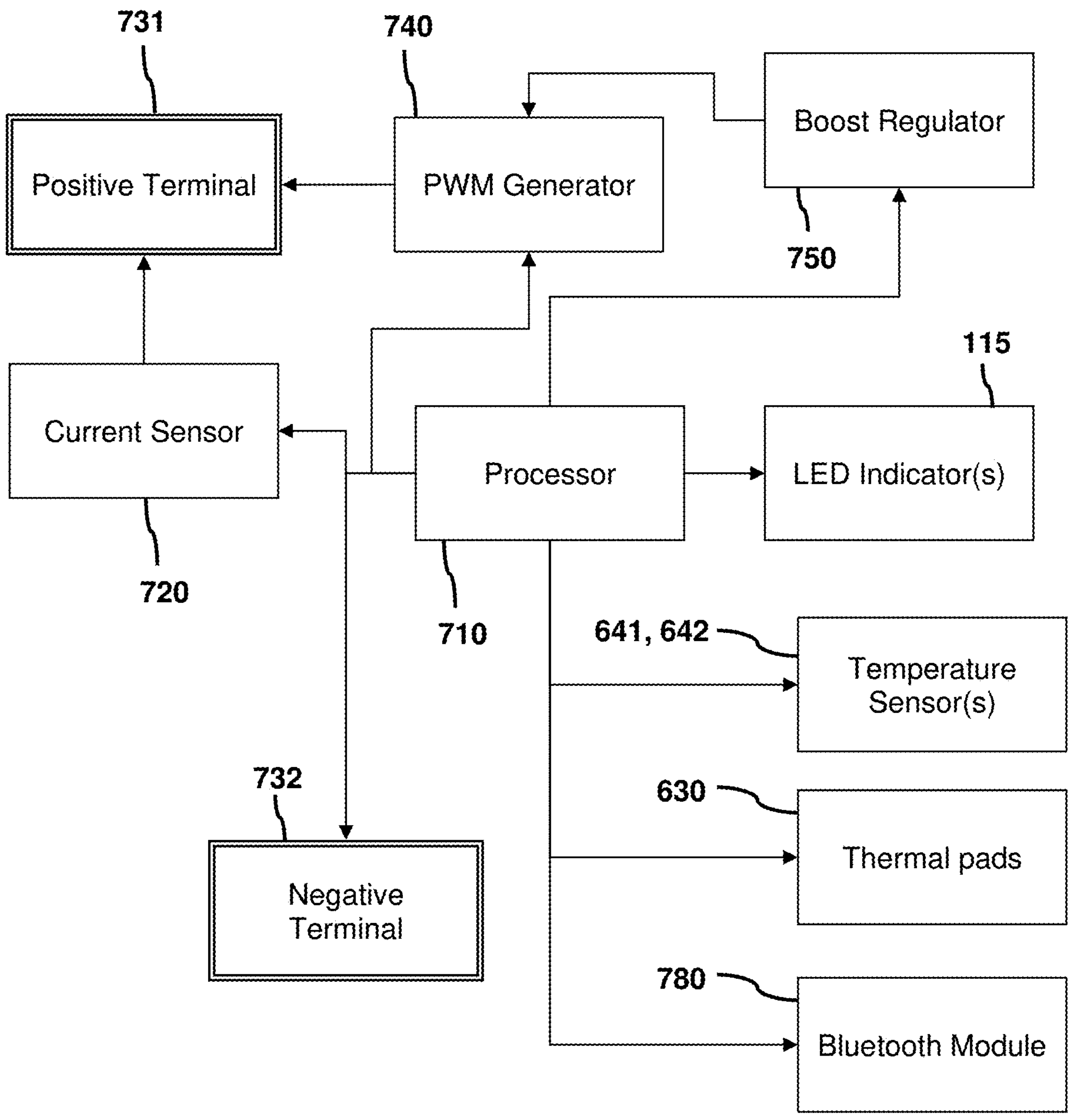
FIG. 7 is a system block diagram of a knee mounting device adapted to stimulate the acupoint of a patient for treating osteoarthritic pain in accordance with certain embodiments of the present disclosure.

Referring to FIG. 7, an exemplary system block diagram of the knee brace 100 is illustrated. The knee mounting device 100 further comprises a processor 710, a PWM generator 740, a boost regulator 750, one or more temperature sensors 641, 642, a current sensor 720, one or more LED indicators 115, and a Bluetooth module 780.

The PWM generator 740 is configured to generate a pulse stimulation signal and couple the pulse stimulation signal to the plurality of contacts 620 for stimulating the acupoint. In certain embodiments, the PWM generator 740 is positioned in the upper assembly 110, and preferably on the circuit board 610. In previous studies, usually, the TENS currents are in the mA range and are too strong to bear by most people. In some cases, continuous stimulation of the same area using a TENS device may cause burn and sharp pain to the patient. This is caused by the mA range of TENS currents, which usually elicits a strong pulse with a stressful and painful sensation on the patient. In certain embodiments, as provided in the present disclosure, the pulse stimulation signal has a constant current of not more than 120 μA, and preferably the constant current is between 20 μA and 60 μA. In certain embodiments, the pulse stimulation signal is a square wave with a pulse width of 50 milli-second to 200 milli-second, and preferably the pulse width is between 100 milli-second and 120 milli-second. After performing TENS treatment, muscular contraction will eventually lead to increased muscular resistance. Therefore, if the PWM generator 740 uses a constant voltage approach, the current would diminish with the progression of the TENS treatment and the therapeutic effects nullified eventually. To provide undiminished current, constant TENS current mode will have to be used, thereby the therapeutic effects are not affected upon continuous use of the knee mounting device 100.

The shape of the lower body differs depending on each patient, therefore it may be beneficial if the plurality of contact pads 620 has a resilient structure. For example, each of the plurality of contact pads 620 may include a resilient member, such as a spring or a piston. The plurality of contact pads 620 should be capable of coupling electric signals to the patient. Therefore, the plurality of contact pads 620 are made of a low resistance conductive material, such as copper, aluminum, gold, nickel, other metallic material, or any combination thereof.

The first contact pad 621 is electrically connected to the PWM generator 740 for coupling the pulse stimulation signal, and the second contact pad 622 is electrically connected to a low reference voltage. Particularly, the PWM generator 740 is configured to generate a pulse stimulation signal at a positive terminal 731, and the negative terminal 732 completes the circuit through the patient by connecting to the GND or a low reference voltage. As the second contact pad 622 is coupled to the negative terminal 732, the current flow from the second contact pad 622 to the first contact pad 621 through the T-36 acupoint 12. So, the second contact pad 622 is relatively larger and longer and could cover any variation in length of the leg wearing the knee mounting device 100.

The Bluetooth module 780 is configured to operate according to the Bluetooth wireless protocol for transmitting and receiving signals from a portable device or a computer device using Bluetooth or other wireless communication protocols. A hand-held mobile controlling module may be used to communicate with the knee mounting device 100 using the Bluetooth module 780, so that the caregiver or therapist can formulate stimulation procedures, treatment plans and collect measurement data. Although a Bluetooth module 780 is depicted, it is apparent that the Bluetooth module 780 can be replaced by other communication devices without departing from the scope and spirit of the present disclosure.

The one or more temperature sensors 641, 642 obtain temperature readings of areas proximate to the one or more thermal pads 630 and areas underneath the knee mounting device 100 to ensure that the temperature is ranged between 36° C. and 40° C. The current sensor 720 is provided for detecting an electric current flowing through the patient via the plurality of contacts 620. The current sensor 720 is a high-precision current sensor that can detect constant current in the μA range. The processor 710 is configured to monitor and adjust the one or more thermal pads 630 and the PWM generator 740 continuously based on the temperature detected by the one or more temperature sensors 641, 642 and the electric current detected by the current sensor 720. Preferably, the processor 710 is a microcontroller embedded in the circuit board 610. In other alternative embodiments, the processor 710, provided in the upper assembly 110, may be a discrete control device, a computation system implemented by a portable device, a personal computer, a cloud-based server, or other electronic devices capable of performing computation. The boost regulator 750 is configured to generate reference voltages for the PWM generator 740 and other electronic components. In certain embodiments, the boost regulator 750 generates voltage ranges from 5V to 120V.

The illustrated embodiments are non-limiting examples of the knee mounting device 100. It is also appreciated that the knee mounting device 100 may have different shapes, configurations, and arrangements. For example, the knee mounting device 100 may be a TENS device configured in the form of a tightening device, an adjustable strap, a fastening device, or the like, mountable on the patient's knee, which is adapted to stimulate the ST-36 acupoint 12. Another example provides a TENS device being integrated with a garment or other wearable devices. The TENS device may partially cover or fully cover the lower body.

Generally, the TENS device may include a sleeve 140 having a kneecap opening 141 located to enwrap the patient's knee and place the plurality of contacts 620 on top of the ST-36 acupoint 12; a plurality of contacts 620 arranged on an underside 510 of the sleeve 140 for contacting the ST-36 acupoint 12 on the lower leg; a PWM generator 740 configured to generate a pulse stimulation signal and couple the pulse stimulation signal to the plurality of contacts 620 for stimulating the ST-36 acupoint 12; and one or more thermal pads 630 arranged on the underside 510 of the sleeve 140 for applying thermal treatment to an area proximate to the ST-36 acupoint 12. Similar to the knee mounting device 100 described above, the plurality of contacts 620 in the TENS device includes at least a positive terminal 731 and a negative terminal 732. The positive terminal 731 is electrically connected to the PWM generator 740 for coupling the pulse stimulation signal, and the negative terminal 732 is electrically connected to a low reference voltage. The kneecap opening 141 receives the kneecap 11 when the sleeve 140 is worn by the patient for defining an anchor position, and the positive and negative terminals 731, 732 are positioned relative to the anchor position to contact the ST-36 acupoint 12 accurately. Particularly, the positive and negative terminals 731, 732 are dimensioned to cover individual variations of the ST-36 acupoint 12, with the negative terminal 732 being physically larger than the positive terminal 731.

Figure 8:
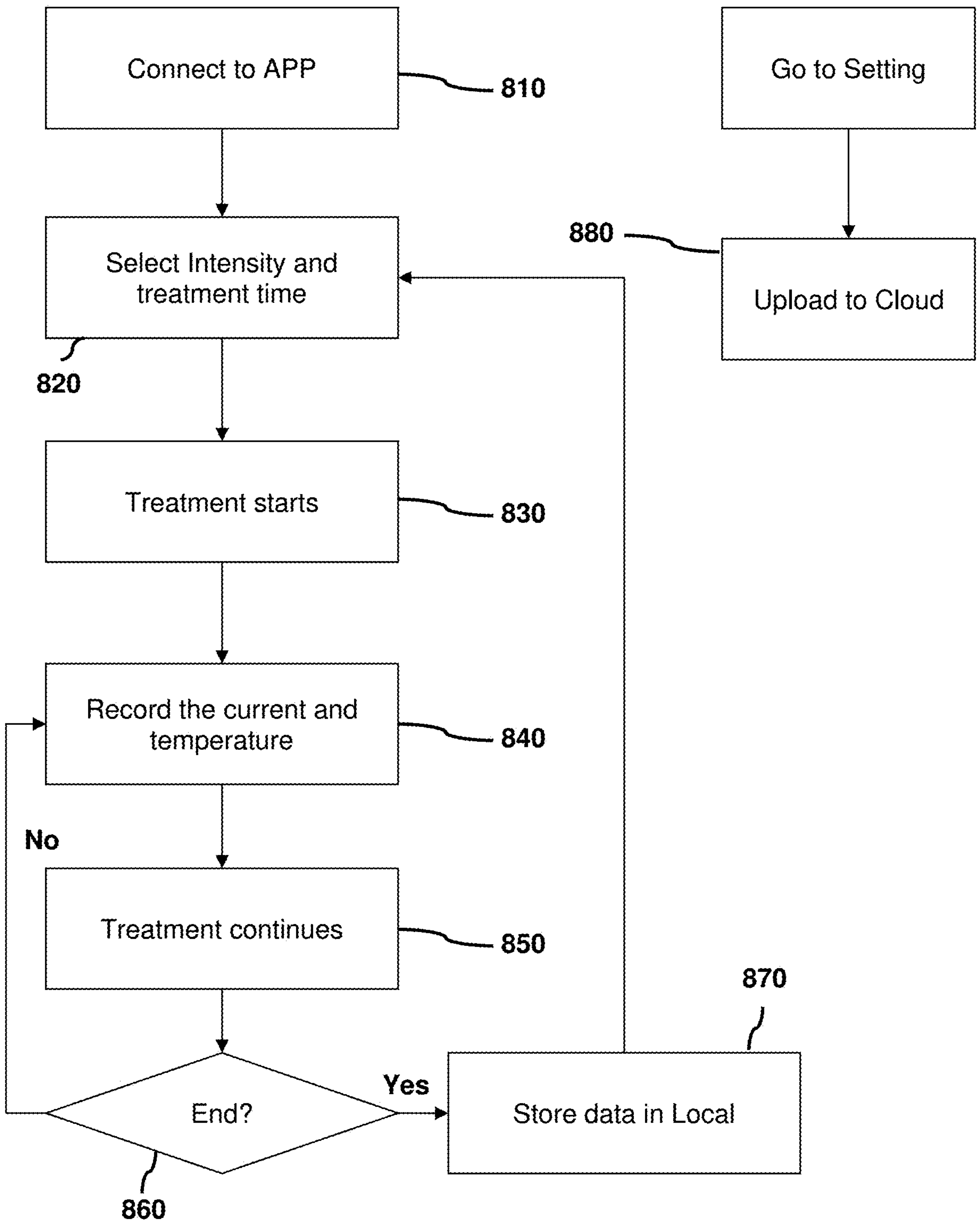
FIG. 8 is a flowchart illustrating the method of stimulating the acupoint of a patient for treating osteoarthritic pain in accordance with certain embodiments of the present disclosure.

FIG. 8 is a flowchart illustrating the method of stimulating acupoints of a patient using the knee mounting device 100 of the present disclosure for treating or relieving osteoarthritic pain. The caregiver can first properly put the knee mounting device 100 on the knee of the patient, such that the plurality of contacts 620 and the one or more thermal pads 630 arranged on the underside of the knee mounting device 100 are properly contacted the ST-36 acupoint 12. When it is done, the knee mounting device 100 should be connected to the app 810 for control and data logging by wireless communication, such as Bluetooth. The caregiver uses the app to select the intensity and treatment time 820. Then the treatment is started 830. The electric current and temperature readings of areas proximate to the thermal pads 630 are recorded 840 while the treatment continues 850. The processor 710 regularly determines whether the operation treatment should continue 860, and when the treatment is completed, the electric current and temperature readings recorded are transmitted via Bluetooth technology and stored in the memory 870 of the portable controlling device or computer. The output of these data can be seen in the Apps from the controlling device or computer system. In certain embodiments, these data are presented as diagrams and graphs. The caregiver can anytime upload the stored data to a cloud system 880, which can be accessed by the caregiver, medical practitioners, or therapists.

Figure 9A:
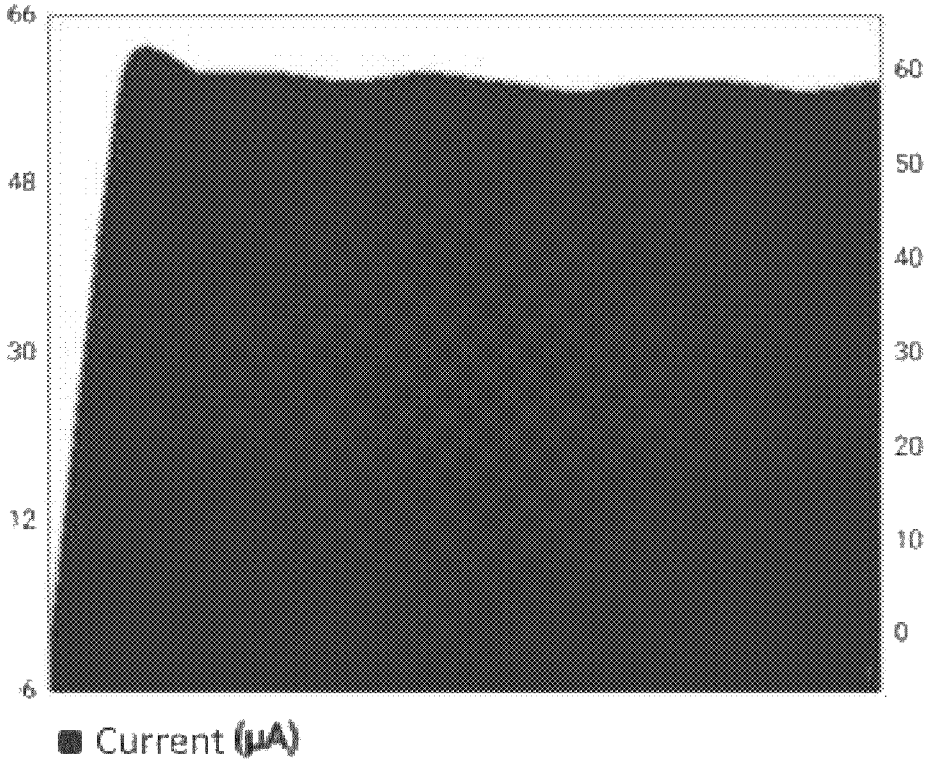
FIG. 9A is a graph showing the current output over time of the knee mounting device in accordance with certain embodiments of the present disclosure.

FIG. 9A shows the current output over time of the knee mounting device as measured by the current sensor 720 during operation. One of the features of the TENS stimulation is to provide a constant current to the acupoint to ensure that the muscular contraction will not lead to an increased muscular resistance. In the example, the current output is maintained at around 60 μA.

Figure 9B:
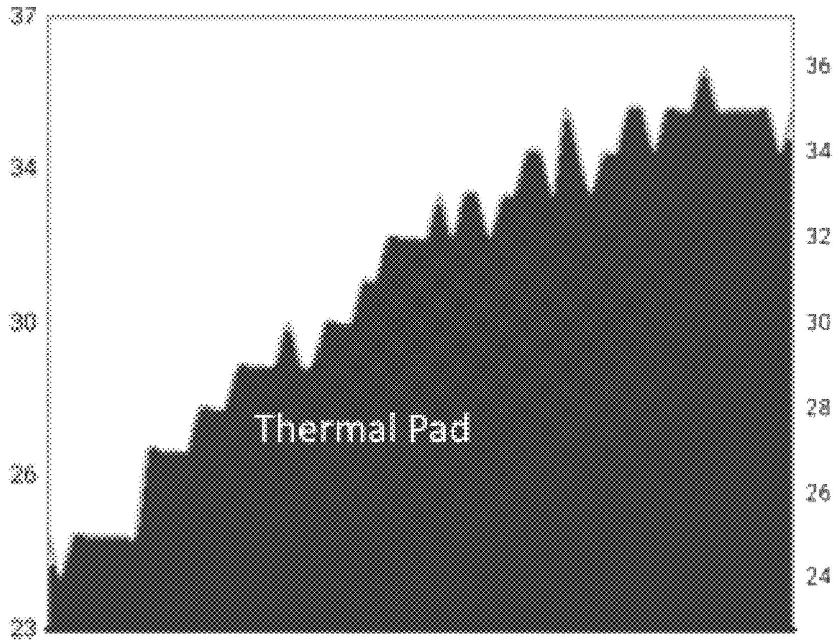
FIG. 9B is a graph showing the temperature readings of output from the thermal pad in accordance with certain embodiments of the present disclosure.

FIG. 9B shows the temperature readings of the output from the one or more thermal pads 630. This is the target output temperature as defined by the processor 710, which can be measured from the downside of the one or more thermal pads 630.

Figure 9C:
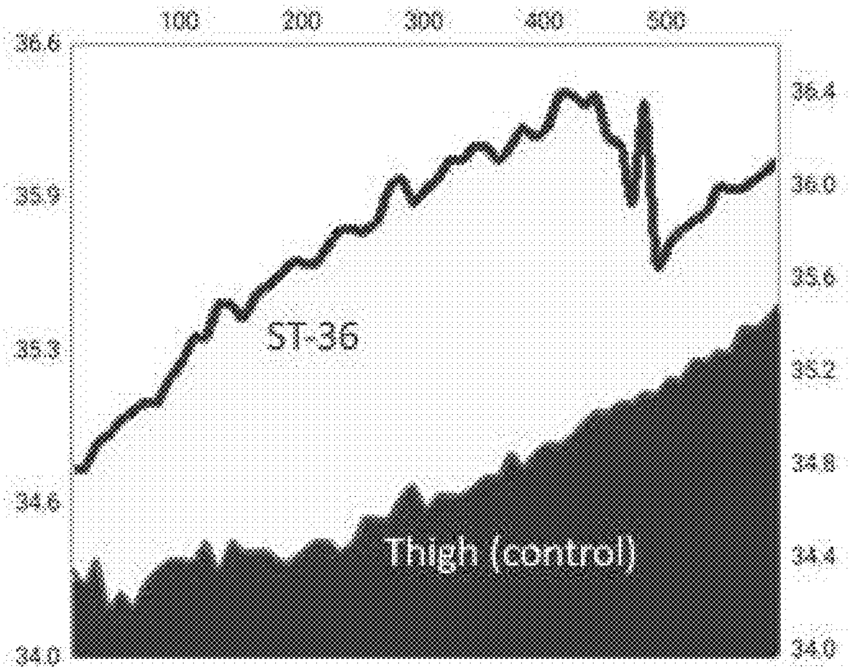
FIG. 9C is a graph showing the temperature readings of areas proximate to the ST-36 acupoint and the knee in accordance with certain embodiments of the present disclosure.

FIG. 9C shows the temperature readings of areas proximate to the ST-36 acupoint 12 and the knee respectively. The temperature of the areas proximate to the ST-36 acupoint 12 is measured by the one or more temperature sensors 641, while the temperature of the knee is measured by the second temperature sensor 642 near the upper assembly 110. The temperature of the knee as measured by the second temperature sensor 642 is used as a control.

A clinical trial was organized to test the efficiency of the knee mounting device 100 of the present disclosure. 33 patients with osteoarthritic pain were recruited to perform the clinical trial (Table 1 shows the demographic data). There are three selection criteria for the patients:

Criterion 1: the patient should be aged between 50-80 years old.

Criterion 2: the patient's systolic blood pressure should be less than 140 mmHg.

Criterion 3: the patient should have persistent knee and joint pain, i.e., with Western Ontario and McMaster Universities Osteoarthritis Index (WOMAC) and Oxford Knee Score (OKS) over 20 points.

Criterion 4: the patient should not have heart disease, implanted pacemaker, diabetes, gout, paralysis, or malignant tumor.

TABLE 1 demographic data of the patients recruited to perform the clinical trial

| Age | 51-55 | 56-60 | 61-65 | 66-70 | 71-75 | 76-80 |
|---|---|---|---|---|---|---|
| Male | 0 | 0 | 1 | 4 | 0 | 0 |
| Female | 1 | 3 | 8 | 9 | 6 | 1 |

In order to determine the effectiveness of the knee mounting device 100 of the present disclosure, the degrees of pain, as well as stiffness and how much that affect the quality of living of each patient, were assessed by the following 3 tests:

Test 1: OKS was used to access the effectiveness of the TENS treatment delivered by the knee mounting device 100 on the ST-36 acupoint 12.

Test 2: WOMAC scale was used to evaluate the condition of the patient with osteoarthritis of the knee, including pain, stiffness, and physical functioning of the joints.

Figure 10:
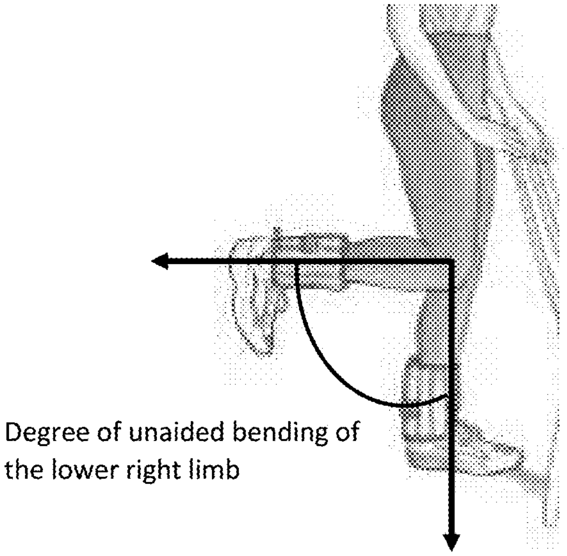
FIG. 10 shows the degree of unaided bending of the right lower limb for assessing the effects of the knee mounting device of the present disclosure.

Test 3: Flexor angle measurement: the degree of unaided bending of the right lower limb was measured by a goniometer using the right knee joint as the center point to gauge if there is an improvement in the stiffness as well as possible swelling of the knee joint, as conceptually illustrated in FIG. 10.

Figure 11:
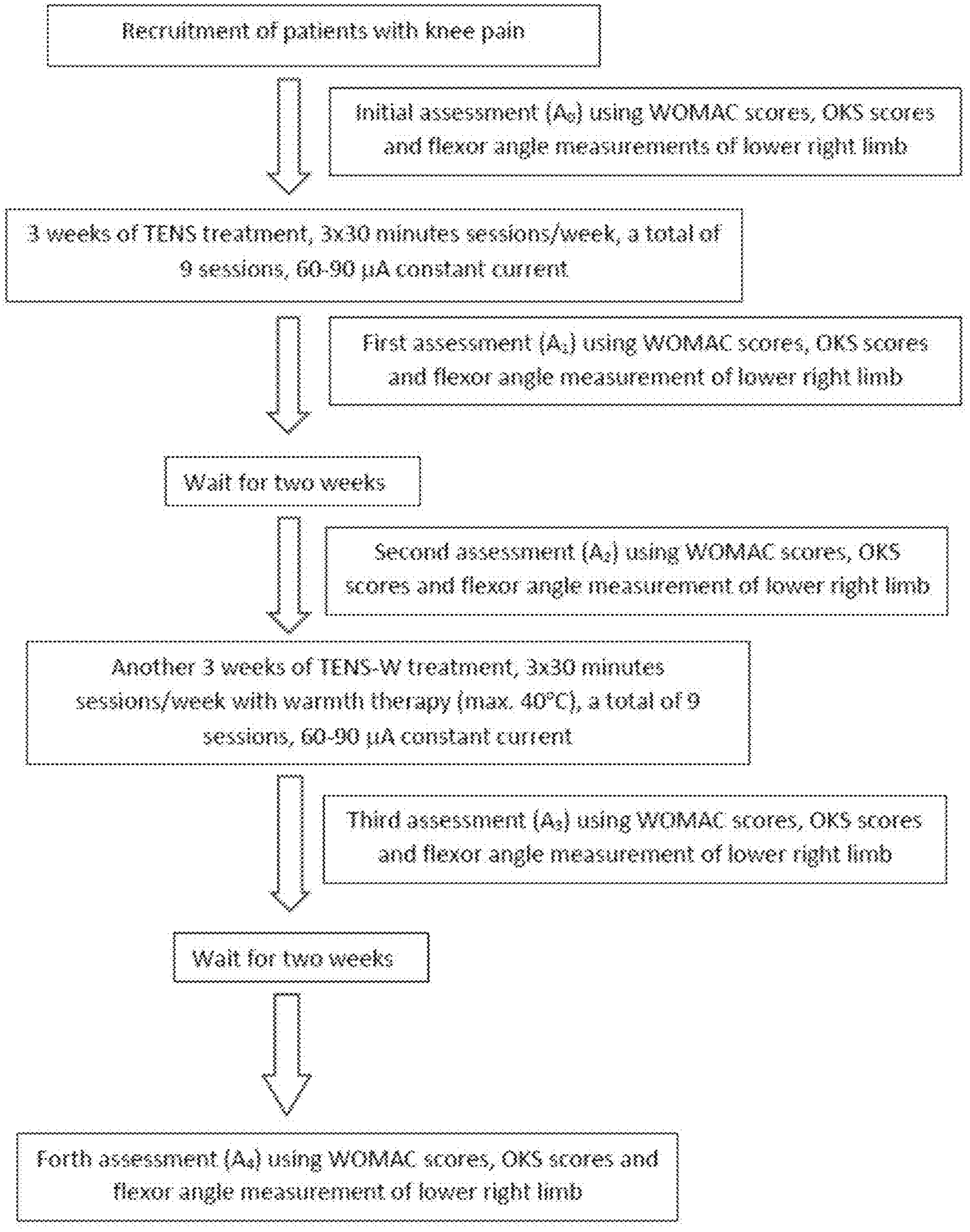
FIG. 11 is the schedule of the treatment and assessment for the patient under the clinical trial.

The schedule of the treatment and assessment for the patient under the clinical trial are shown in FIG. 11. The clinical trial comprises (1) continuous TENS treatments for 3 weeks, with three 30-minute sessions each week; (2) a break from TENS treatment for 2 weeks; (3) continuous TENS treatments with thermal modalities for another 3 weeks, with three 30-minute sessions each week; and (4) a break from TENS treatment for 2 weeks. In the clinical trial, due to the COVID-19 pandemic, a final round of clinic trial was suspended, and only the initial assessment ($A_0$), second assessment ($A_2$), and final assessment ($A_4$) were performed. The results are summarized in Table 2 below.

TABLE 2

Measurement result of the assessments

| | Bend angles (degrees) measured | Average OKS scores (max = 60) | Average WOMAC scores (max = 96) |
|---|---|---|---|
| $A_0$ | 90.0 | 35.5 | 42.8 |
| $A_2$ | 95.3 | 31.1 | 44.6 |
| $A_4$ | 97.5 | 27.7 | 34.9 |

With reference to the bend angle measurements, it is found that the average scores of the subjects increased from the initial 90.0 degrees to 95.3 degrees ($A_0$ against $A_2$) after the intervention studies with TENS-only treatment. It can be interpreted that the ability of subjects to bend their lower right limb in an unaided manner increased. This could be a combination of several factors such as an increase in muscle strength, a decrease in stiffness, and swelling of the joints. Further studies are needed to verify these confounding factors. With the addition of thermal modalities ($A_0$ against $A_4$), the bend angels were further increased, from 90.0 degrees to 97.5 degrees. There is an 8% increase in bend angle after TENS treatment with thermal modalities.

With reference to the OKS scores, it is found that the description of pain (through answering the questionnaires) by the subjects after TENS only treatment ($A_0$ against $A_2$) decreased from 35.5 to 31.1, after the intervention studies. With the additional thermal modalities ($A_0$ against $A_4$), the OKS scores further decreased to 27.7. With TENS treatment and thermal modalities, there is a decrease of around 22% in knee pain description.

With reference to the WOMAC scores, it is found that the scores increased from 42.8 to 44.6 ($A_0$ against $A_2$). Whether this increase was due to psychological or other factors are currently unknown. With the resumption of treatment and the addition of thermal modality, the scores decreased in a similar manner as the other parameters. There is a decrease of about 18% in this set of scores which measured stiffness and knee pain.

Other beneficial effects experienced by the patients after TENS treatment with thermal modalities were mostly related to the alleviation of stiffness as well as pain at the various joints of the body. Particularly, it is noticed that the stiffness of the frozen shoulder was alleviated in some patients, and the stiffness of the whole body was alleviated and increased muscular strength of both legs in some other patients.

The knee mounting device 100 of the present disclosure helps caregiver and patient to find the correct location of ST-36 acupoint 12 easily. After a total of 2 times of 3 weeks of intervention (3 sessions of 30 minutes each week) with an intermission of 2 weeks after the TENS only treatment and before TENS treatment with thermal modalities started, TENS and thermal treatment of the knee through the ST-36 acupoint 12 is successful in reducing pain scores and allow subjects to be able to have more flexion in their lower right limbs. Increased flexibility in other parts of the body and increased muscle strength of the other lower left limbs were also observed.

This illustrates the knee mounting device or the TENS device with thermal modalities for treating osteoarthritic pain in accordance with the present disclosure. It will be apparent that variants of the above-disclosed and other features and functions, or alternatives thereof, may be combined into many other different configurations and systems. The present embodiment is, therefore, to be considered in all respects as illustrative and not restrictive. The scope of the disclosure is indicated by the appended claims rather than by the preceding description, and all changes that come within the meaning and range of equivalency of the claims are therefore intended to be embraced therein.

LIST OF REFERENCES

There follows a list of references that are occasionally cited in the specification. Each of the disclosures of these references is incorporated by reference herein in its entirety.

[1] Zhang Y Q and Niu J B. Shifting gears in osteoarthritis research towards symptomatic osteoarthritis. Arthritis Rheumatol. 2016; 68: 1797-1800.

2] Overview of VA research on Arthritis, U.S. Department of Veterans Affairs, https://www.research.va.gov/topics/arthritis.cfm (accessed on Jun. 14, 2022).

[3] Lee A, Tsang C, Wong W and Wong S. An evidence-based approach to managing osteoarthritis in the primary care setting. The Hong Kong Practioner: The journal of the Hong Kong College of Family Physicians. 2004; 26:11.

[4] Whitney Alexandra, Common Side Effects of Analgesics, www.healthprep.com/articles/medications/common-side-effects-analgesics/

What is claimed is:

1. A knee mounting device for providing transcutaneous electrical nerve stimulation (TENS) treatment, the knee mounting device configured to be coupled to a patient's knee to locate and stimulate Zusanli (ST-36) acupoint region of the patient transcutaneously for treating or relieving osteoarthritic pain, the knee mounting device comprising:

- a lower assembly mountable onto a leg portion under a kneecap of the patient, wherein the lower assembly comprises:
  - a plurality of contacts arranged on an underside of the lower assembly for contacting the ST-36 acupoint region on the lower leg; and
  - one or more thermal pads arranged on the underside of the lower assembly for applying thermal treatment to an area proximate to the ST-36 acupoint region;
- an upper assembly mountable on a thigh of the patient, wherein the upper assembly comprises a pulse width modulation (PWM) generator configured to generate a pulse stimulation signal and couple the pulse stimulation signal to the plurality of contacts for stimulating the ST-36 acupoint region; and
- a sleeve adapted to connect the upper assembly and the lower assembly, wherein the sleeve is provided with a kneecap opening configured to be located to enwrap the patient's knee and place the plurality of contacts on top of the ST-36 acupoint region, wherein the ST-36 acupoint region comprises an area within +/−2 centimeters of a target location on the lower leg, the target location being defined by a position relative to an anchor position of the knee mounting device, and wherein the kneecap opening is configured to receive the kneecap when the knee mounting device is worn by the patient for defining the anchor position,
- wherein the knee mounting device further comprises:
  - one or more temperature sensors for obtaining temperature readings of areas proximate to the one or more thermal pads and areas underneath the knee mounting device;
  - a current sensor for detecting an electric current flowing through the patient via the plurality of contacts; and
  - a processor provided in the upper assembly, wherein the processor is configured to monitor and adjust the one or more thermal pads and the PWM generator continuously based on the temperature readings detected by the one or more temperature sensors and the electric current detected by the current sensor.

2. The knee mounting device of claim 1, wherein the plurality of contacts comprises a first contact pad and a second contact pad, wherein the first contact pad is electrically connected to the PWM generator for coupling the pulse stimulation signal, and the second contact pad is electrically connected to ground (GND).

3. The knee mounting device of claim 2, wherein the first and the second contact pads are positioned relative to the anchor position of the knee mounting device to contact the ST-36 acupoint region.

4. The knee mounting device of any one of claims 1 to 3, wherein the pulse stimulation signal has a constant current of not more than 120 μA, thereby therapeutic effects are not affected upon continuous use of the knee mounting device.

5. The knee mounting device of any one of claims 1 to 3, wherein the pulse stimulation signal is a square wave with a pulse width of 50 milli-second to 200 milli-second.

6. The knee mounting device of claim 1, wherein each of the one or more thermal pads comprises a winding of a thermally conductive material for delivering thermal energy to the ST-36 acupoint region and the area proximate to the ST-36 acupoint region with a temperature up to 40° C.

7. The knee mounting device of claim 1, wherein the upper assembly comprises a Bluetooth module configured to operate according to the Bluetooth wireless protocol for transmitting and receiving wireless signals.

8. The knee mounting device of claim 1, wherein the upper assembly and the lower assembly are electrically connected together using flexible cables.

9. The knee mounting device of claim 1, wherein the upper assembly and the lower assembly each comprises fastening means for applying a tension to hold the upper assembly and the lower assembly on the thigh and the lower leg of the patient respectively, wherein the fastening means comprise a strap and a strap fastener.

10. The knee mounting device of claim 1, wherein the sleeve is made of an elastic material selected from the group consisting of natural rubber, silicone, latex, nylon, elastic textile, and cotton.

11. The knee mounting device of claim 1, wherein the sleeve is dimensioned to partially cover or encircle the kneecap and to allow an accurate localization of the ST-36 acupoint.

12. The knee mounting device of claim 1 further comprising a vibrator arranged on the underside of the lower assembly for providing psychological effects to the patient.

13. The knee mounting device of claim 4, wherein the constant current is between 20 μA and 60 μA.

14. The knee mounting device of claim 5, wherein the pulse width is between 100 milli-second and 120 milli-second.

* * * * *